May 27, 1958 A. W. MAFFEY Plant Pat. 1,713

PEACH TREE

Filed Oct. 11, 1957

WITNESS

Addison E. Avery

INVENTOR

Albert W. Maffey

Webster & Webster

ATTYS.

United States Patent Office

Plant Pat. 1,713
Patented May 27, 1958

1,713

PEACH TREE

Albert W. Maffey, Modesto, Calif.

Application October 11, 1957, Serial No. 689,739

1 Claim. (Cl. 47—62)

This discovery relates to a new and distinct variety of peach tree which bears freestone fruit particularly desirable for dessert use by reason of fine texture and excellent flavor, and for freezing as it is relatively resistant to discoloration by oxidization. The fruit is medium to large size, generally white fleshed with red next to the stone, and has a light green skin (with scant down) partially overspread—adjacent the top or base—with an attractive rose color.

As compared to the Nectar peach (United States Plant Patent No. 86), and which is popular for table use, the herein claimed variety bears general resemblance in flavor, color, and size, but is distinctively characterized by a considerably later harvest season.

As compared to the freestone Strawberry peach (unpatented), the present variety has a later harvest season, a more austere flavor, and a greener external or skin color.

The present variety of peach tree originated as a chance seedling discovered by me in the yard of the residence on my ranch located near Modesto, Stanislaus County, California; the area being subject to my control, continued observation, and cultivation.

Subsequent to discovery of such peach tree I maintained it under careful observation and it bore fruit which obviously had desirable characteristics, and was a variety evidencing commercial potential. Thereupon, I grafted the variety on a nectarine root stock on my ranch located as aforesaid, and when such asexual reproduction came into bearing it was true to the parent tree in all respects.

Figure 1:
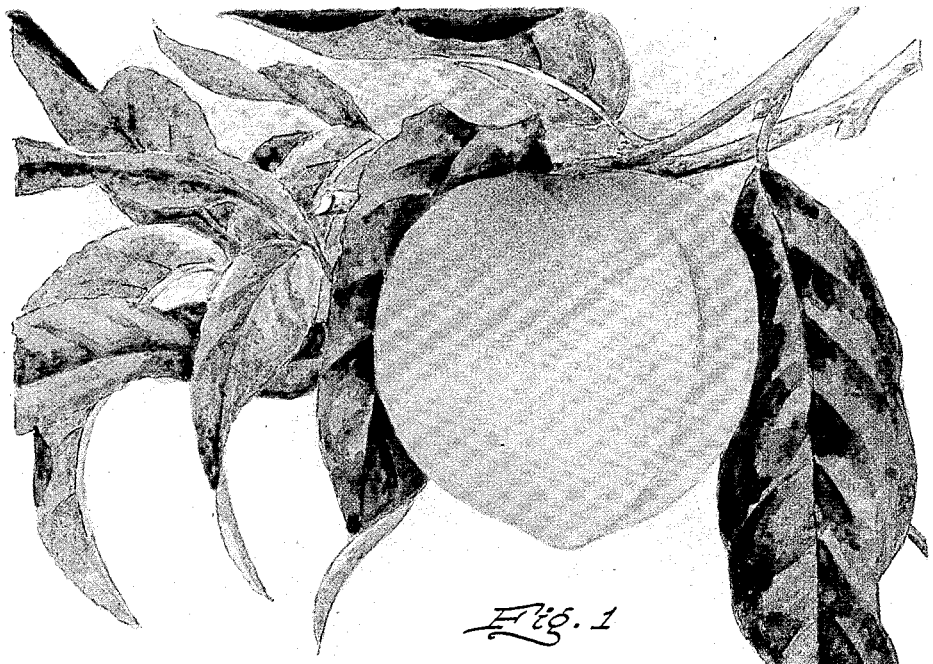
Fig. 1 is an elevation of one of the fruit, together with twigs and leaves.
Figure 2:
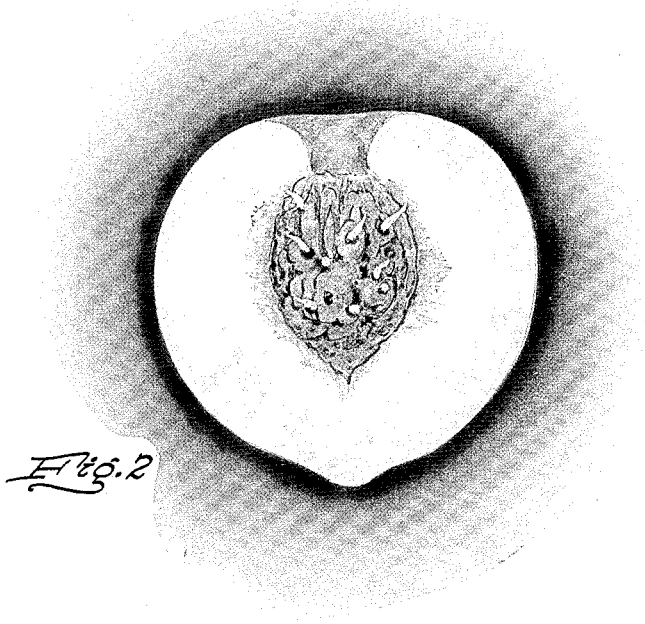
Fig 2 is a sectional elevation of one of the fruit, with the stone exposed.

Referring now more specifically to the pomological details of this new and distinct variety of peach tree, the following is an outline description thereof; all major plate identifications being by reference to Maerz and Paul Dictionary of Color:

Tree:
- *Size.*—Large.
- *Vigor.*—Vigorous.
- *Growth.*—Spreading.
- *Density.*—Dense.
- *Form.*—Round topped.
- *Hardiness.*—Hardy
- *Production.*—Productive.
- *Bearing.*—Regular bearer.

Trunk:
- *Size.*—Medium.
- *Texture.*—Medium.

Branches:
- *Size.*—Medium.
- *Texture.*—Medium
- *Color.*—Green—brown.
- *Lenticels.*—Medium number.

Leaves:
- *Size.*—Medium—large. Average length, 5½" to 7¼". Average width, 1¼" to 2".
- *Form.*—Lanceolate; acuminate; acutely pointed.
- *Thickness.*—Medium.
- *Texture.*—Slightly rugose.
- *Margin.*—Glandular; crenate.
- *Petiole.*—Short; thick.
- *Glands.*—Average number—two. Usually opposite; medium size; globose; green; usually positioned on apical petiole, occasionally basal on blade.
- *Stipules.*—Dehiscent.
- *Color.*—Mature leaves: top side—medium to dark green (23–L–7); under side—lighter green (22–J–6).

Flower buds:
- *Size.*—Medium.
- *Length.*—Medium.
- *Form.*—Conic; appressed.
- *Pubescence.*—Pubescent.

Flowers:
- *Blooming period.*—Medium compared with other varieties.
- *Size.*—Medium.
- *Color.*—Salmon Fruit:
- *Date of first picking in average season.*—August 27th.
- *Date of last picking in average season.*—September 11th.
- *Size.*—Uniform. Medium—large. Average diameter axially, 2½" to 3". Average transversely in suture plane, 2⅝" to 2¾".
- *Form.*—Uniform; symmetrical; globose.
- *Suture.*—Distinct—shallow. Extends from base to beyond but discontinuous at apex; slight depression beyond pistil point.
- *Ventral surface.*—Rounded; strongly lipped toward base throughout both sides; lips nearly equal.
- *Cavity.*—Flaring; rounded; sometimes abrupt; slightly elongated in suture plane, with suture showing on one side. Average depth, ½". Average breadth, ¾" to 1¼".
- *Base.*—Rounded.
- *Apex.*—Short; mammiform.
- *Pistil point.*—Apical.

Skin:
- *Thickness.*—Medium.
- *Texture.*—Medium.
- *Tenacity to flesh.*—Free.
- *Tendency to crack.*—None.
- *Down.*—Scant; short; does not roll up when rubbed.
- *Color.*—Pale or light green (17–K–3—18–K–3, shading to 18–K–1), overspread at the top with a rose blush (4–K–8 deepening to 6–L–7).

Flesh:
- *Texture.*—Medium; fine.
- *Fibers.*—Few; fine; tender.
- *Ripens.*—Even.
- *Flavor.*—Austere; subacid.
- *Aroma.*—Distinct.
- *Eating quality.*—Good.
- *Color.*—White (9–A–1), shading outwardly toward the skin with a greenish cast (18–D–1); streaked with red (4–J–6 to 1–L–8) next to stone. Surface of pit cavity—red (4–J–6), with white fibers.

Stone:
- *Type.*—Free; parts from flesh smoothly, but retains a number of fibers.

*Size.*—Large. Average length, 1½″ to 1⅞″. Average breadth, 1 1/16″ to 1 3/16″. Average thickness, 1″ to 1 1/16″.

*Form.*—Oval.

*Hilum.*—Oval.

*Apex.*—Acute.

*Sides.*—Equal.

*Surface.*—Irregularly furrowed toward apex; pitted toward base.

*Ridges.*—Rounded; continuous.

*Pits.*—Elongated.

*Ventral edge.*—Thick, without wing throughout.

*Dorsal edge.*—Narrow, with deep narrow groove throughout.

*Tendency to split.*—Slight.

*Color.*—Brown (14–C–12), shading to purple (5–A–5), particularly near the base.

Use: Dessert; freezing.

Keeping quality: Good.

Shipping quality: Medium.

The tree and its fruit herein described may vary in slight detail due to climatic and soil conditions under which the variety may be grown.

The following is claimed:

A new and distinct variety of peach tree, as illustrated and described, characterized by medium to large sized freestone fruit having generally white flesh streaked with red next to the stone, and of fine texture and flavor; further characterized by skin having scant down and a light green color overspread adjacent the base with rose; additionally characterized—as compared to the Nectar peach—by general resemblance in size, flavor, and color, but having a later harvest season, occurring on the average in the latter part of August and the early part of September; and still further characterized—as compared to the freestone Strawberry peach—by such later harvest season, a more austere flavor, and a greener skin color.

No references cited.